United States Patent
Stern et al.

[11] Patent Number: 5,368,592
[45] Date of Patent: Nov. 29, 1994

[54] ARTICULATED SYSTEMS FOR CARDIAC ABLATION

[75] Inventors: Roger A. Stern, Cupertino; Stuart D. Edwards, Los Altos; Jerome Jackson, Sunnyvale, all of Calif.

[73] Assignee: EP Technologies, Inc., Sunnyvale, Calif.

[21] Appl. No.: 126,126

[22] Filed: Sep. 23, 1993

Related U.S. Application Data

[63] Continuation of Ser. No. 868,010, Apr. 13, 1992.

[51] Int. Cl.⁵ .............................................. A61N 1/40
[52] U.S. Cl. ...................................... 606/33; 604/95; 403/90
[58] Field of Search ............. 606/39, 33; 609/269, 609/95; 128/789, 785, 786, 804; 403/90

[56] References Cited

U.S. PATENT DOCUMENTS

| | | | |
|---|---|---|---|
| 3,433,510 | 3/1969 | Hulterstrum | 403/90 X |
| 3,665,928 | 5/1972 | Del Guercio | 604/95 |
| 3,674,014 | 7/1972 | Tillander | 604/95 X |
| 3,691,788 | 9/1972 | Mazzotti | 403/90 X |
| 3,841,769 | 10/1974 | Bowerman | 403/90 |
| 3,957,241 | 5/1976 | Morris et al. | 403/129 X |
| 4,154,246 | 5/1979 | LeVeen | 128/786 X |
| 4,409,993 | 10/1983 | Furihata | |
| 4,945,912 | 8/1990 | Langberg | 606/33 X |
| 4,979,948 | 12/1990 | Geddes et al. | 606/33 |
| 5,108,368 | 4/1992 | Hammerslag et al. | 604/95 |

*Primary Examiner*—Peter A. Aschenbrenner
*Attorney, Agent, or Firm*—Ryan, Kees & Hohenfeldt

[57] ABSTRACT

An improved assembly for steering and orienting a functional element at the distal end of a catheter tube holds the functional element with its major axis aligned with the axis of the catheter tube for convenient steering to a tissue site. The mechanism can also pivot the functional element in response to an external force to orient the major axis of the functional element generally parallel to the plane of the tissue site, without bending the catheter tube.

16 Claims, 5 Drawing Sheets

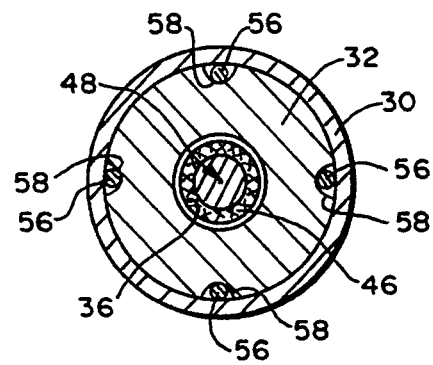
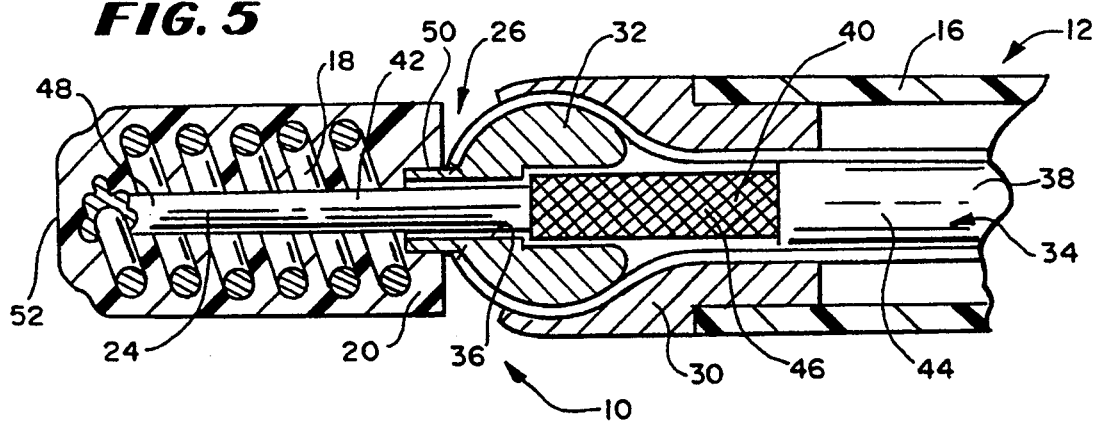
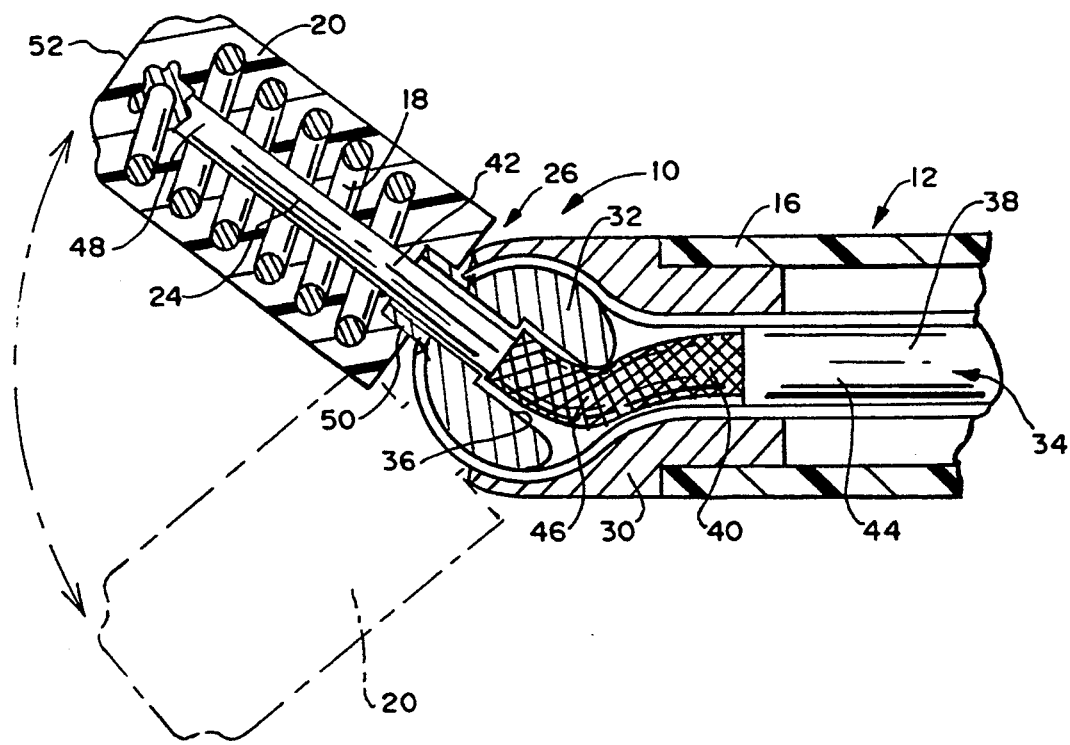

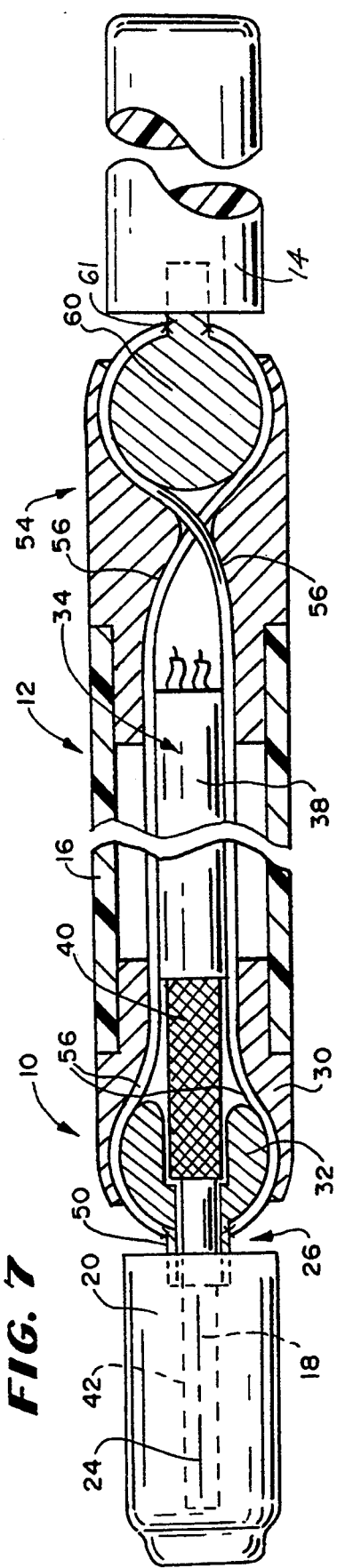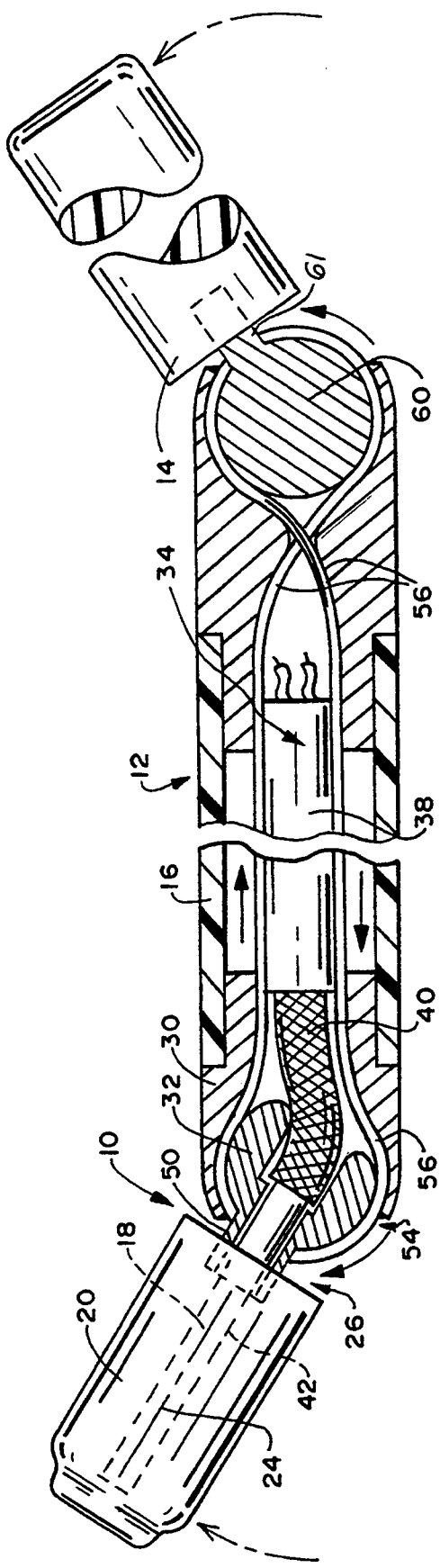

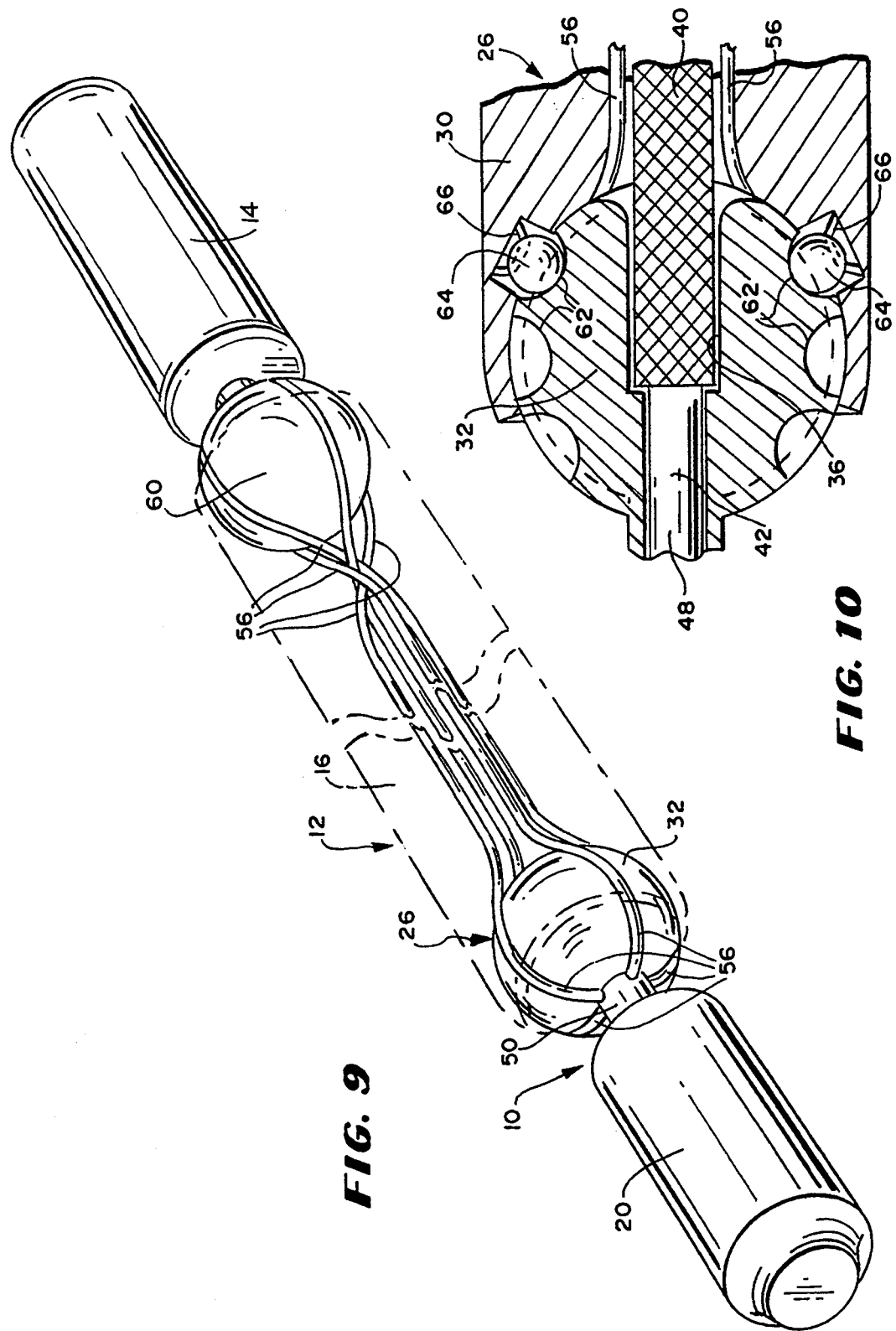

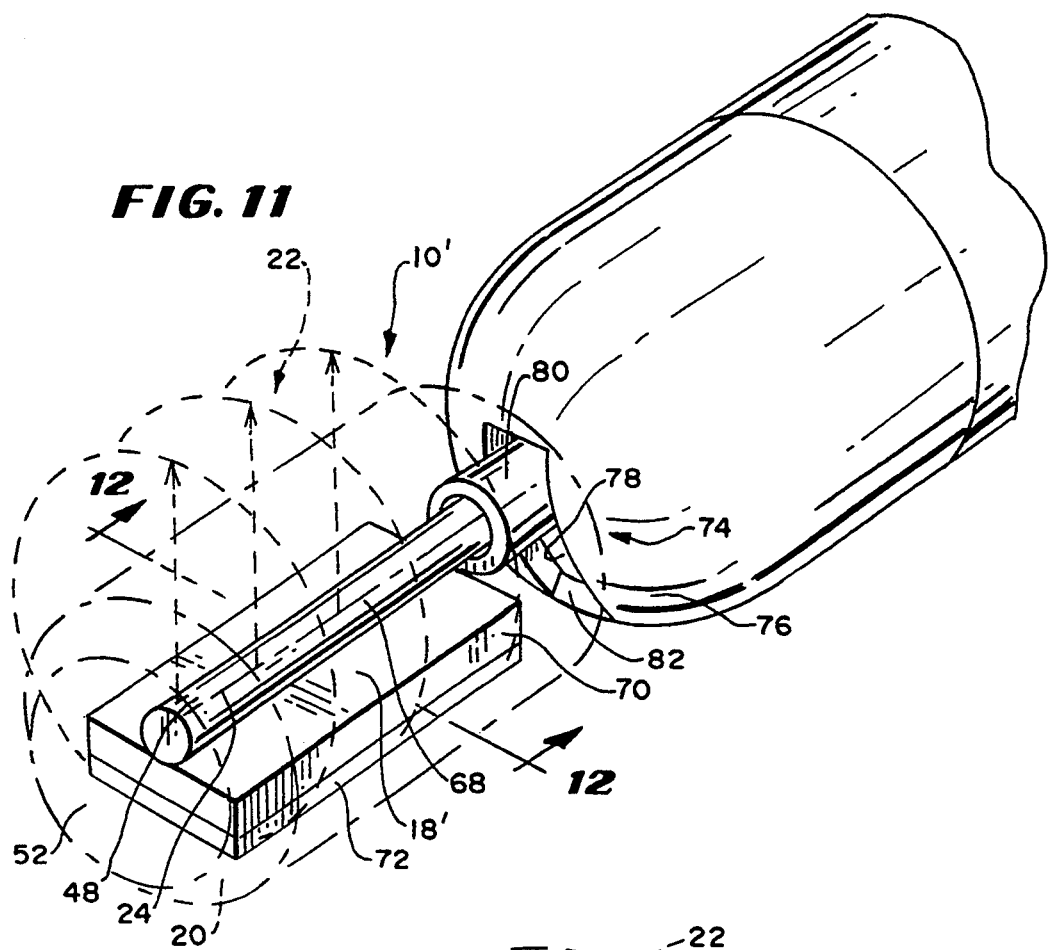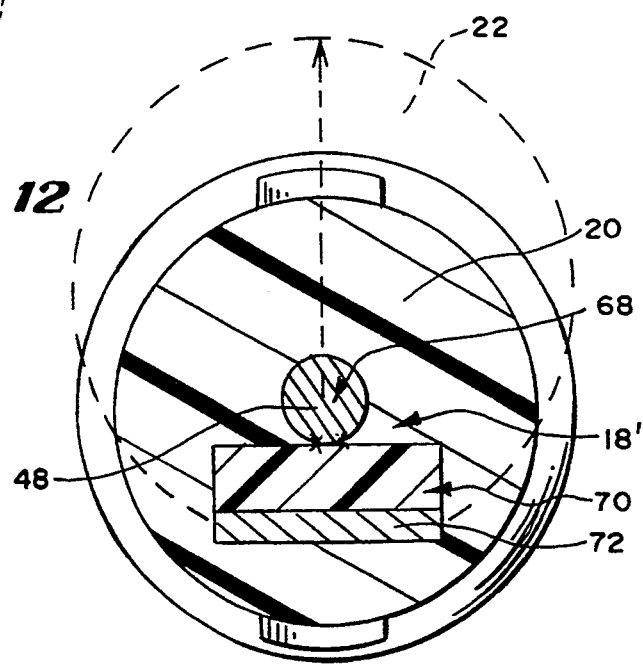

ARTICULATED SYSTEMS FOR CARDIAC ABLATION

This is a continuation of copending application(s) Ser. No. 868,010 filed on Apr. 13, 1992.

FIELD OF THE INVENTION

The invention generally relates to cardiac ablation catheters and systems. In a more specific sense, the invention relates to catheters that use microwave energy to ablate ventricular and atrial tachycardia foci for the treatment and control of cardiac arrhythmias.

BACKGROUND OF THE INVENTION

Physicians make use of catheters today in medical procedures to gain access into interior regions of the body to ablate tissue areas. It is important for the physician to be able to accurately steer the catheter to the ablation site. Once at the site, it is important for the physician to control the emission of energy within the body used to ablate the tissue.

The need for accurate steering and precise control over the catheter is especially critical during procedures that ablate tissue within the heart. These procedures, called electrophysiology therapy, are becoming increasingly more widespread for treating cardiac rhythm disturbances, called arrhythmias.

During these procedures, a physician steers a catheter through a main vein or artery (which is typically the femoral artery) into the interior region of the heart that is to be treated. The physician then further manipulates a steering mechanism to place the electrode carried on the distal tip of the catheter into direct contact with the tissue that is to be ablated. The physician directs radio frequency (RF) energy from the electrode tip through the tissue to an indifferent electrode to ablate the tissue and form a lesion.

Some clinicians have suggested the use of microwave energy for cardiac ablation. For example, Langberg U.S. Pat. No. 4,945,915 proposes the use of a helical microwave antenna fed by a coaxial line to thermally ablate cardiac tissue. The radiation heating patterns that microwave energy propagate can, in theory at least, form lesions that are deeper than the lesions formed by the conductive heating patterns generated by conventional RF energy.

The ability of microwave energy to form deeper lesions also raises challenges in antenna system design. To gain all the benefits of using microwave energy, the clinician must be able to control the distribution of heating patterns propagated at the intended lesion site.

A microwave antenna generates an electromagnetic field that radiates in a radial plane, perpendicular to the axis of the antenna. The radial field has only minimal intensity forward of the tip of the antenna.

The radial field orientation of a microwave antenna is not well suited for use in conventional cardiac ablation procedures. In cardiac ablation using RF, the physician is accustomed to placing the ablation electrode tip down upon the ablation site, i.e., perpendicular to the site. Orienting a microwave antenna in this manner directs only a small percentage of the energy field upon the ablation site. Most of the energy radiates into the blood pool and serves no useful purpose. The benefits of microwave energy ablation are lost.

Ablation systems and processes using microwave energy will not find widespread clinical use, if they cannot be made and controlled to direct the major portion of the radial electromagnetic field upon the ablation site. They will also fail to find widespread use, if the microwave antenna cannot be conveniently steered and positioned to the proper orientation at desired ablation site.

SUMMARY OF THE INVENTION

One aspect of the invention provides an improved assembly for steering and orienting a functional element at the distal end of a catheter tube. The functional element can be an active electrode or antenna for ablating tissue using RF, laser, and the like. The functional element can also be a passive monitoring element, like one or more mapping electrodes, MAP elements, or ultrasound electrodes.

A mechanism supports the functional element at the distal end of the catheter tube. The mechanism holds the functional element with its major axis aligned with the axis of the catheter tube for convenient steering to a tissue site. The mechanism can also pivot the functional element in response to an external force to orient the major axis of the functional element generally parallel to the plane of the tissue site, without bending the catheter tube.

In one embodiment, the pivot mechanism includes a ball and socket joint.

In a preferred embodiment, steering wires are connected to the pivot mechanism and to a remote actuator mechanism that is accessible to the user for applying the external force.

In one embodiment, the pivot mechanism is restricted to a predefined field of movement. It can also including detents for releasable retaining the pivot mechanism in one or more preselected positions.

The pivot mechanism that embodies the features of the invention is ideally suited for use in association with a microwave ablation antenna. The pivot mechanism allows the user to lay the major axis of the antenna parallel to the ablation site. In this orientation, the ablation site is exposed to the full radial field propagated by the antenna.

The pivot mechanism that embodies the features of the invention is also ideally suit for use with antenna and the like that are unidirectional. The pivot mechanism can restrict the movement of the unidirectional element to assure its proper orientation with the tissue site.

BRIEF DESCRIPTION OF THE DRAWINGS

FIG. 4 is a sectional view of the end assembly taken generally along line 4—4 in FIG. 1;

FIG. 5 is a side section view of the end assembly positioned as shown in FIG. 1;

FIG. 6 is a side section view of the end assembly positioned as shown in FIGS. 2 and 3;

FIGS. 7 and 8 are side section view of an embodiment of the end assembly having an associated steering mechanism;

FIG. 9 is a perspective view of the end assembly and associated steering mechanism;

FIG. 10 is side section view of an embodiment of the end assembly having an associated pivot detent mechanism;

FIG. 11 is a perspective view of an embodiment of an end assembly in association with a unidirectional antenna element; and FIG. 12 is a section view of the unidirectional antenna element taken generally along line 12—12 in FIG. 11.

DESCRIPTION OF THE PREFERRED EMBODIMENTS

Figure 1:
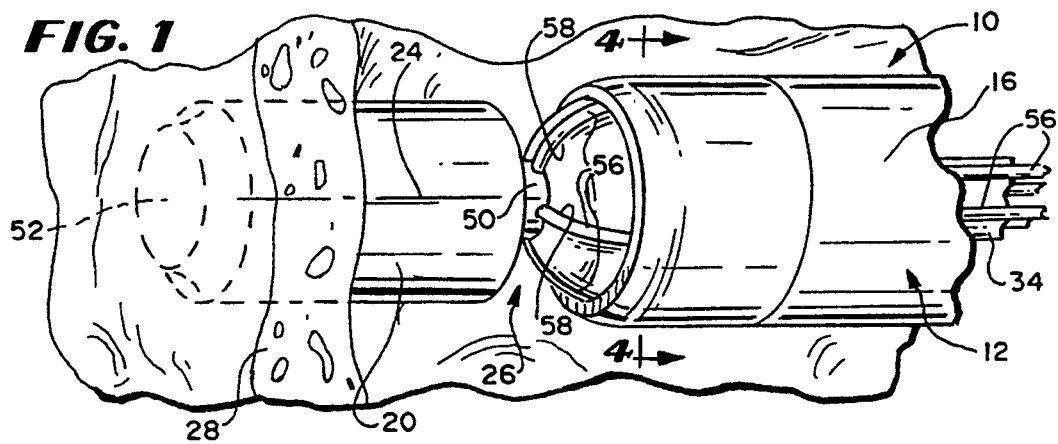
FIG. 1 is a perspective view of a catheter having an end assembly that embodies the features of the invention, with the end assembly holding the major axis of the associated functional element in a position axially aligned with the axis of the catheter body.

FIG. 1 shows an articulated antenna assembly 10 that embodies the features of the invention. The antenna assembly 10 is located at the distal end of a catheter 12.

The catheter 12 includes a handle 14 (shown diagrammatically in FIG. 9) and a guide body 16. The guide body 16 is flexible with its proximal end attached to the handle 14. The antenna assembly 10 is attached to the distal end of the guide body 16.

In use, the catheter provides electrophysiology therapy in the interior regions of the heart.

When used for this purpose, a physician grips the handle 14 and maneuvers the guide body 12 through a main vein or artery (which is typically the femoral arterial) into the interior region of the heart that is to be treated. The physician then further steers the antenna assembly 10 to place it in contact with the tissue that is to be ablated. The physician directs energy to the antenna assembly 10 to ablate the tissue contacted.

In the illustrated embodiment shown in FIGS. 1 to 9, the antenna assembly includes a helical microwave antenna 18 (best shown in FIGS. 5 and 6). The antenna 18 is encapsulated in a potting compound 20. Preferably, the potting compound 20 includes a material (like diamond or sapphire) that has the combined characteristics of (i) a high dielectric constant; (ii) low microwave energy loss; and (iii) high thermal conductivity. The compound 20 provides a high dielectric constant for the antenna 18. By minimizing the loss of microwave energy by the antenna 18, the compound 20 also maximizes the propagation of the desired radiation heating patterns about the antenna 18. The compound 20 has high thermal conductivity that dissipates any undesirable conductive heat patterns about the antenna 18.

Further details of the compound 20 are found in co-pending patent application entitled "Steerable Microwave Antenna Systems For Cardiac Ablation that Minimize Tissue Damage and Blood Coagulation Due to Conductive Heating Patterns," which shares the same filing date and assignee as this application.

Figure 2:
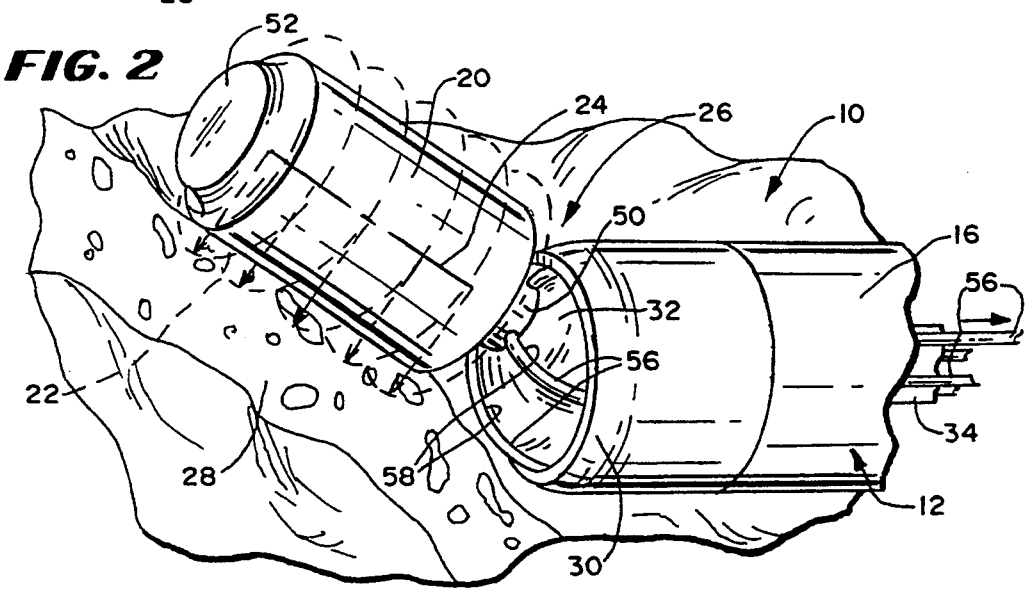
FIGS. 2 and 3 are perspective views the end assembly shown in FIG. 1 with it pivoted to lay the major axis of the associated functional element against the tissue.

The microwave antenna 18 propagates an electromagnetic field 22 that radiates in a plane perpendicular to the major axis 24 of the antenna 18 (as FIG. 2 diagrammatically shows in phantom lines). There is very little field propagation forward of the distal tip of the antenna 18.

According to one aspect of the invention, the antenna assembly 10 includes means 26 for pivoting the antenna 18 relative to the end of the guide body 12 without bending the guide body 12. The pivot means 26 orients the antenna 18 so that its major axis 24 lays generally parallel to the surface of the tissue 28 to be ablated. This orientation exposes the tissue 28 to the maximum intensity of the radial field 22 the antenna 18 propagates.

The pivot means 26 can be variously constructed. In the illustrated embodiment, the pivot means 26 takes the form of an articulated jointed assembly attached to the distal end of the guide body 12. The jointed assembly 26 includes a socket housing 30 and a ball 32 pivotally carried within the socket 30.

The antenna assembly 10 includes a coaxial cable 34 that extends within the guide body 12, into the socket housing 30, and through a passage 36 within the ball 32 for attachment to the antenna 18. The coaxial cable 34 has three, functionally different regions 38, 40, and 42.

The first region 38 constitutes the majority of the coaxial cable. It is enclosed within an outer insulation sheath 44 and runs along the guide body 16. In a preferred embodiment, the sheath 44 has an outer diameter of about 0.06 inch.

In the second region 40, the outer sheath 44 is absent, leaving a metallic mesh shield 46 that surrounds the core conductor wire 48. In an preferred embodiment, the mesh shield 46 has an outer diameter of about 0.054 inch. The second region 40 extends into the socket housing 30 and within the ball passage 36. With the removal of the relatively bulky outer sheath 44, the second region 40 is significantly more flexible than the first region 38 and accommodates movement of the ball 32 within the socket housing 30 (as FIG. 6 shows).

The third region 42 is at the distal end of the cable 34. It passes from the ball passage 36 and joins the helical antenna 18. There is no surrounding sheath 44 or shield 46 in the third region 42, leaving the core conductor 48 of the cable 34 exposed.

In a preferred embodiment, the core conductor 48 is silver coated copper having an outer diameter of about 0.018 inch. With the antenna 18, the third region 42 is encapsulated within the compound 20.

A shaft 50 joins the compound-encapsulated antenna 18 to the ball 32 for unified pivotal movement in a continuous multidirectional field.

The user can pivot the compound-encapsulated antenna 18 by placing its distal tip 52 against the ablation site and applying a lateral force upon the catheter guide body 12 (see FIG. 1). With the tip 52 against the tissue, the lateral force will cause the compound-encapsulated antenna 18 to pivot and lay flat against the tissue 28 at the ablation site, without otherwise bending the guide body 12.

Figure 3:
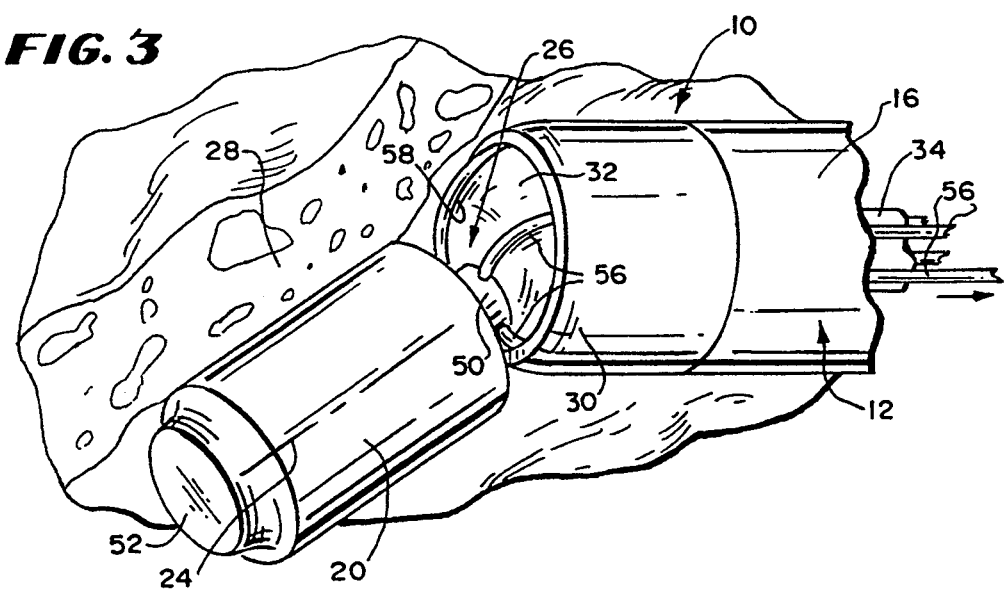

As shown in FIGS. 1 to 3, the jointed assembly 26 accommodates pivotal movement in any plane. When pivoted, the compound encapsulated antenna 18 will lay either as shown in FIG. 2 or as shown in FIG. 3, depending upon the topography of the adjacent tissue 28.

In a preferred arrangement, the jointed assembly 26 also includes a steering mechanism 54 for pivoting the ball 32 without the need to apply lateral force on the guide body 12.

The steering mechanism 54 can be variously constructed. In the illustrated embodiment, the steering mechanism 54 includes four steering wires 56 that are attached to the ball shaft 50 at 90 degree intervals. The steering wires 56 are retained in recessed grooves 58 in the ball 32.

As FIGS. 7 to 9 shown, the steering wires 56 extend from the shaft 50, through the grooves 58 and the guide body 12 to join a remote 60. Ball joint 60 is integral with steering lever 61 which is in turn connected to catheter handle 14.

In this arrangement, the user can move the steering lever 60 up, down, left, and right and pivot the ball 32 to move of the compound-encapsulated antenna 18 in the same direction. As before, this pivotal movement occurs without bending the catheter guide body 12.

FIG. 10 shows another embodiment of the jointed assembly 26. In this embodiment, the ball 32 includes detents 62 formed at preselected pivot positions. The socket housing 30 includes bearings 64 that are biased by washers 66 to nest within the detents 62. The nesting between the bearings 64 and the detents 62 retains the ball 32 in a series of predefined pivot positions. Additional pivot force upon the ball 32 releases the nested bearings 64 and detents 62. In this way, the user can pivot the compound-encapsulated antenna 18 within a range of preselected positions.

FIG. 11 shows another embodiment of a steerable antenna assembly 10' that embodies the features of the invention. The assembly in FIG. 11 includes a unidirectional microwave antenna 18'.

The unidirectional antenna 18' comprises a sandwich of three layers that are encapsulated in the compound 20. The first layer 68 comprises the core conductor 48 of the coaxial cable 34 (i.e., its third region 42). The second layer 70 is a dielectric material, called the dielectric plane. The third layer 72 is an energy conducting ground plane.

As FIGS. 11 and 12 show, the antenna 18' propagates an electromagnetic field 22' that radiates in a single direction from the major axis 24 of the core conductor 48. There will be little, if any, field emission radially from the ground plane 72, as well as forward of the tip 52 of the antenna 18'.

Preferable, the antenna assembly 10' also includes a unidirectional pivot mechanism 74 for assuring that the antenna 18' is properly oriented with respect to the ablation site. In the illustrated embodiment, the unidirectional pivot mechanism 74 includes a jointed assembly comprising a socket housing 76 and a ball 78 like that previously described. However, unlike the fully articulated jointed assembly 26 shown in FIGS. 1 to 3, the jointed 74 assembly in FIG. 11 is restricted to movement in a single range of positions.

In FIG. 11, the shaft 80 of the ball 78 is retained within a partial slot 82. The partial slot 82 allows pivotal movement of the ball 78 within the socket housing 76 only in a plane that will orient the unidirectional antenna 18' upon the tissue with its conductor core 48 facing the tissue. This aims the unidirectional field of the antenna 18' solely at the ablation site. Because all the power supplied to the antenna 18' is directed in a single direction, the power applied to the tissue is effectively doubled, when compared to an omnidirectional antenna 18, like that shown in FIGS. 5 and 6. Furthermore, the unidirectional antenna 18' minimizes the exposure of the surrounding blood pool to the electromagnetic field, because the dielectric plane 70 blocks propagation of the field radially from the ground conductor layer 72. Undesired effects of blood heating, like coagulation, are thereby minimized.

It should be appreciated that other microwave antenna structures (for example, an omnidirectional whip antenna) can be similarly attached to a pivot assembly at the end of a catheter to achieve the benefits of the invention.

The inventions provide a steerable microwave antenna assembly that maximizes the propagation of radiation heating patterns for deep lesion formation.

The inventions are also applicable for supporting any functional element at the distal end of the catheter body 12. For example, instead of supporting a microwave antenna 18, the joint assembly can support other active elements or electrodes for tissue ablation using RF, laser, and the like. The joint assembly can also support passive monitoring elements, like one or more mapping electrodes, MAP elements, or ultrasound electrodes.

Whatever the particular function of the distal element may be, the joint assembly holds the functional element with its major axis aligned with the major axis of the catheter body 12 for convenient steering to the tissue site. The joint assembly then pivots the functional element in response to an external force to orient its major axis generally parallel to the plane of the tissue site without bending the catheter body 12.

Various features and benefits of the inventions are set forth in the following claims.

We claim:

1. An end assembly attached to the distal end of a catheter tube comprising
a socket positioned on the distal end of said assembly
a rotatable ball pivotally supported in said socket and extending distally therefrom,
a functional element having a major axis, said functional element being supported on said ball with its major axis aligned with the axis of the catheter tube for steering to a tissue site and for pivoting the functional element in response to an external force to orient the major axis of the functional element generally parallel to the plane of the tissue site without bending the catheter tube,
a cable extending within the catheter tube into said socket and through a passage within said ball, the distal end of said cable being attached to said functional element, and
a plurality of steering wires connected to said ball and to a remote actuator mechanism accessible to the user for applying the external force.

2. An assembly according to claim 1
wherein the functional element is mounted on a shaft projecting from said ball.

3. An assembly according to claim 1
and further including means for restricting the movement of the ball to a predefined field of movement.

4. An assembly according to claim 1
and further including means for releasably retaining the ball in at least one preselected position.

5. An assembly according to claim 1
wherein the functional element is an antenna for ablating tissue.

6. An assembly according to claim 5
wherein the functional element is a microwave antenna.

7. An assembly according to claim 5
wherein the functional element is a helical microwave antenna.

8. An end assembly supported on the distal end of a catheter tube comprising
a socket housing Joined to the distal end of the catheter tube,
a ball element carried in the socket housing for pivotal movement within it,
a functional element attached to the distal end of the ball element for unified pivotal movement with It at the distal end of the catheter,
a wire extending through the catheter tube and the ball element for conveying energy to the functional element, and
the ball element including an interior passage for the wire from the catheter tube to the attached functional element, and steering means connected to the ball element and to a remote actuator mechanism accessible to the user for applying en external force to pivot the ball element, the steering means including at least one steering wire attached to the ball element and the remote actuator mechanism.

9. An assembly according to claim 8 and further including means on the ball element and the socket housing for releasable retaining the ball element in at least one preselected position.

10. An assembly according to claim 9 wherein the retaining means includes at least one detent on one of the ball element and the socket housing and at least one spring biased bearing element on the other one of the ball element and the socket housing that releasable nests within the detent when the ball element assumes the preselected position.

11. An assembly according to claim 8 and further including means for restricting the range of pivotal movement of the ball element within the socket housing.

12. An assembly according to claim 8 wherein the functional element is an electrode for ablating tissue.

13. An assembly according to claim 12 wherein the functional element is a microwave antenna.

14. An assembly according to claim 13 wherein the functional element is a helical microwave antenna.

15. An assembly according to claim 10 wherein said ball comprises a plurality of detentes.

16. An assembly according to claim 4 wherein said steering means comprises four wires connected to said ball element at 90° intervals.

* * * * *